United States Patent
Rubin et al.

(10) Patent No.: US 7,632,650 B2
(45) Date of Patent: Dec. 15, 2009

(54) DIAGNOSTICS AND THERAPEUTIC USES OF TOPORS

(75) Inventors: Eric H. Rubin, Belle Mead, NJ (US); Ahamed Saleem, Highland Park, NJ (US); Zeshaan Rasheed, Piscataway, NJ (US); Paul Haluska, Jr., Rochester, MN (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 303 days.

(21) Appl. No.: 11/671,041

(22) Filed: Feb. 5, 2007

(65) Prior Publication Data

US 2008/0038731 A1    Feb. 14, 2008

Related U.S. Application Data

(63) Continuation-in-part of application No. 10/339,924, filed on Jan. 9, 2003, now abandoned.

(60) Provisional application No. 60/346,953, filed on Jan. 9, 2002.

(51) Int. Cl.
*G01N 33/53* (2006.01)

(52) U.S. Cl. .......................................... 435/7.23; 435/6
(58) Field of Classification Search ........................ None
See application file for complete search history.

(56) References Cited

U.S. PATENT DOCUMENTS 5,798,266 A * 8/1998 Quay et al. ................... 436/64

OTHER PUBLICATIONS

OMIM entry # 609507 downloaded on May 16, 2009 from NCBI web site url>>> http://www.ncbi.nlm.nih.gov/entrez/dispomim.cgi?id=609507.*
NCBI Accession No: AF098300 [gi:4566494] with revision history—Apr. 6, 1999-Jun. 22, 1999.
Haluska et al., "Interaction between the N-terminus of human topoisomerase I and SV40 large T antigen", Nucleic Acids Research 1998 26(7):1841-1847.
Zhou et al., "Identification of a novel gene encoding a p53-associated protein", Gene 1999 235:93-101.

* cited by examiner

*Primary Examiner*—Misook Yu
(74) *Attorney, Agent, or Firm*—Licata & Tyrrell P.C.

(57) ABSTRACT

The present invention relates to topors and its association with cancer. Topors antibodies are provided for use in diagnosing cancer based upon the absence of topors in a given cell or tissue sample. The detection of topors nucleic acid molecules in the diagnosis of cancer is also provided.

2 Claims, 6 Drawing Sheets

THYROID   BRAIN
  ADRENAL   HEART
  PANCREAS   KIDNEY
  OVARY   SPLEEN
  UTERUS   LIVER
  PROSTATE   LUNG
  SKIN   SMALL INTESTINE
  PBL   MUSCLE
  BONE MARROW   STOMACH
  FETAL BRAIN   TESTIS
  FETAL LIVER   PLACENTA

*FIG. 9*

```
                          SEQUENCE LISTING

<160> NUMBER OF SEQ ID NOS: 5

<210> SEQ ID NO 1
<211> LENGTH: 20
<212> TYPE: PRT
<213> ORGANISM: Homo sapiens

<400> SEQUENCE: 1

Val Tyr Glu Gly Lys Ala Thr Asp Thr Thr Lys His His Lys Lys Lys
1               5                   10                  15

Lys Lys Lys His
            20

<210> SEQ ID NO 2
<211> LENGTH: 28
<212> TYPE: DNA
<213> ORGANISM: Artificial Sequence
<220> FEATURE:
<223> OTHER INFORMATION: Synthetic primer

<400> SEQUENCE: 2
cgagcaccag cacgataaag agttcgtc                                        28

<210> SEQ ID NO 3
<211> LENGTH: 25
<212> TYPE: DNA
<213> ORGANISM: Artificial Sequence
<220> FEATURE:
<223> OTHER INFORMATION: Synthetic primer

<400> SEQUENCE: 3
tcctgccgac accgacctag ctttc                                           25

<210> SEQ ID NO 4
<211> LENGTH: 26
<212> TYPE: DNA
<213> ORGANISM: Artificial Sequence
<220> FEATURE:
<223> OTHER INFORMATION: Synthetic primer
```

```
<400> SEQUENCE: 4
tgaaggtcgg agtcaacgga tttggt                                          26

<210> SEQ ID NO 5
<211> LENGTH: 24
<212> TYPE: DNA
<213> ORGANISM: Artificial Sequence
<220> FEATURE:
<223> OTHER INFORMATION: Synthetic primer

<400> SEQUENCE: 5
catgtgggcc atgaggtcca ccac                                            24
```

DIAGNOSTICS AND THERAPEUTIC USES OF TOPORS

This application is a continuation-in-part application of U.S. patent application Ser. No. 10/339,924, filed Jan. 9, 2003 now abandoned, which claims priority to U.S. Provisional Patent Application Ser. No. 60/346,953, filed Jan. 9, 2002, the contents of which are incorporated herein by reference in their entireties.

This invention was made in the course of research sponsored by the National Institutes of Health (NIH Grant No. GM59170). The U.S. government may have certain rights in this invention.

BACKGROUND OF THE INVENTION

Topoisomerase 1 (top1) is a DNA binding protein that regulates DNA topology through changing the degree of supercoiling by cutting the DNA strand. Human DNA top1 is a 100 kDa nuclear protein and is the target of an important class of anti-neoplastic agents called camptothecins (CPTs). CPTs are lethal to cells as a result of the formation of DNA-top1-CPT ternary complexes. Relatively little is known about the interaction between top1 and other proteins, even though these interactions are likely important in the cellular functions of top1 and in the cytotoxic mechanisms of camptothecins (Haluska, et al. (1998) *Adv. Enz. Regul.* 38:253-62). Physical interactions have been detected between top1 and two proteins implicated in carcinogenesis, SV40 T antigen and p53 (Haluska, et al. (1998) *Nucleic Acid Res.* 26(7):1841-7; Zhou, et al. (1999) *Gene* 235(1-2):93-101). These findings highlight the potential significance of top1-binding proteins in tumorigenesis.

Using a yeast two-hybrid screen, a novel topoisomerase 1- and p53-binding protein called topors was discovered. Topors is a RING protein that binds to the N-terminus of human top1 (Haluska, et al. (1999) supra). The coding region of topors is deposited under GENBANK Accession Number AF098300. Topors is unique in that it contains both a RING finger and serine and arginine domains in the same polypeptide. Subsequent to the identification of topors, a peptide fragment of topors was identified as a p53-binding protein (Zhou, et al. (1999) supra). Homology searches indicate that the topors RING domain is similar to the RING domain of proteins involved in ubiquitin or SUMO transfer reactions.

Figure 1:
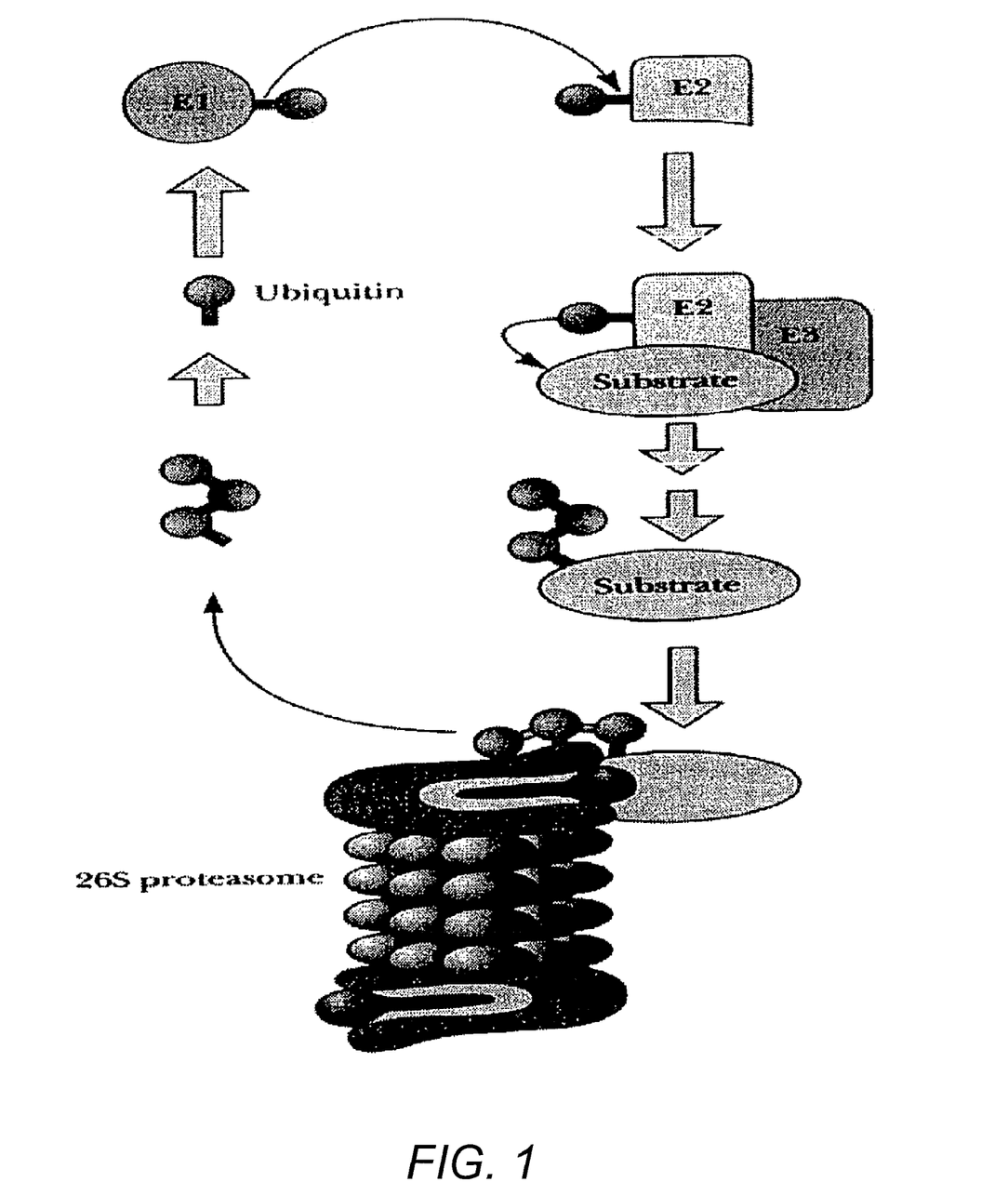
FIG. 1 is a cartoon depiction of protein ubiquitination and sumoylation activities. E1 is the ubiquitin activating enzyme. E2 is the ubiquitin conjugating enzyme. E3 is ubiquitin ligase.

Ubiquitination is critical to cellular function. The conjugated ubiquitin system tags proteins for degradation by proteosomes. As shown in FIG. 1, the ubiquitin activating enzyme activates ubiquitin in the presence of ATP. This enzyme is a single enzyme in most species. The ubiquitin conjugating enzyme contributes to substrate specificity. Ubiquitin ligase also confers substrate specificity and can be a complex of proteins (SCF) or a single protein (c-Cbl). Ubiquitin ligase may transfer ubiquitin directly from the ubiquitin conjugating enzyme to the substrate or form an ubiquitin-conjugate intermediate (see FIG. 1).

SUMO (small ubiquitin-related modifier) proteins are small protein tags that are conjugated to cellular regulator proteins. The regulator proteins include oncogenes and tumor suppressor genes that play key roles in the control of cell growth, differentiation and apoptosis. SUMO conjugation affects the substrates' subcellular localization and stability as well as transcriptional activities. Three different SUMO proteins are conjugated to proteins, SUMO-1, SUMO-2 and SUMO-3. SUMO-1 is conjugated to proteins as a monomer, and SUMO-2 and SUMO-3 are conjugated to proteins as higher molecular weight polymers with SUMO-1 terminating further SUMO addition.

One target of SUMO modification includes proteins involved in formation of the promyclocytic leukemia (PML) nuclear bodies. Acute promyelocytic leukemia, a type of cancer affecting the blood, is characterized by an abnormal block in the development of stem cells. Topors promotes the stability of PML nuclear bodies and perhaps alters their role in transcriptional regulation, cellular proliferation and anti-viral responses. The activity of several transcription factors is altered by sumoylation, including C/EBP proteins, c-Myb, glucocorticoid receptor, androgen receptor, and progesterone receptor. Sumoylation of topoisomerase I alters its localization in the nucleus, and histone deacetylase enzymes are targets of this system. Viral proteins are targets of sumoylation, suggesting that infection and anti-viral cellular defenses may be affected by this system. Protein sumoylation is important in cell cycle progression and genomic stability. Sumoylation may also alter the stability of proteins with polyglutamine repeats involved in neurodegenerative disorders, adding further to the important and diverse roles of this protein modification system.

Since Top1 appears to be an important potential anti-cancer drug target, it is clinically relevant to understand the function and expression of proteins, such as topors, that interact with Top1. It is further important to understand the impact of a topors antibody. The present invention relates to the characterization of topors antibody, further characterization of topors, and the methods of using both topors and topors antibody for cancer diagnostics and therapeutics.

SUMMARY OF THE INVENTION

The present invention is a method for diagnosing cancer in a subject. The method of the invention involves assaying a sample from a subject for the presence or absence of topors, wherein the absence of topors in the sample indicates that the subject has cancer. In particular embodiments, topors is detected using an antibody that binds topors or a nucleic acid molecule that hybridizes to a nucleic acid molecule encoding topors.

DETAILED DESCRIPTION OF THE INVENTION

It has now been found that topors is a candidate tumor suppressor gene similar to p53 and the loss of topors SUMO ligase activity leads to cancer. Topors protein is expressed in most normal tissues and functions as a dual E3 ubiquitin/SUMO ligase in vitro and is the first known protein with this activity. Topors expression is lost in colon and other common human cancers, indicating that topors functions in the cellular response to DNA damage. In this regard, modulation of topors ubiquitin and/or SUMO ligase activities can be useful in diseases associated with alterations in ubiquitin or SUMO pathways, including cancer.

The data provided herein indicate that topors regulates top1 by functioning as an E3-type SUMO ligase for top1. It is known that following exposure to CPT, top1 is sumoylated and ubiquitinated, followed by downregulation in normal cells, but not in tumor cells. Thus, topors is a tumor suppressor.

It is contemplated that the relative lack of topors in tumor cells is involved in this differential response to CPT. In normal cells, DNA damage induces an interaction between topors and top1, resulting in the inactivation of top1 via sumoylation, which facilitates the DNA repair process. However, in cells lacking topors, top1 activity remains unchanged in the presence of DNA damage. This persistence of top1 activity could enhance DNA mutagenesis, a phenotype that is selected for in carcinogenesis. Furthermore, topors protein was detected in normal human tissue samples, but not in matched human tumor tissue specimens from kidney, colon, endometrium and lung tumors. In the tissue specimens where topors protein levels were undetectable in tumor, little if any, topors mRNA was detected. For example, endometrium and colon tumor tissue samples lacking topors protein did not reveal measurable mRNA levels. This finding is consistent with the protein data.

Topors functions as an E3-type SUMO ligase for Top1 and p53 in a purified in vitro system. Furthermore, using a polyclonal antibody developed against recombinant full-length topors, it was demonstrated that the topors protein was expressed in several normal tissues, including bladder, colon, endometrium, kidney, lung, and prostate. Similarly, analysis of a panel of normal tissue cDNAs indicates that topors mRNA is detectable in most normal tissues. The experiments also analyzed 8 matched tumor/normal tissue specimens obtained from patients with colon (4 patients), endometrial (1 patient), lung (1 patient), or renal (2 patients) cancers for actin and topors protein expression. Although actin levels were similar in the tumor and normal tissues, topors protein levels in tumor tissues were either undetectable or significantly less than levels found in corresponding matched normal tissues, for all but one colon tissue pair. Similar results were obtained with quantitative multiplex RT-PCR studies, which indicated loss of topors mRNA expression in 2 colon tumors and one endometrial tumor, relative to matched normal tissue obtained from the same patients. The topors gene maps to chromosome 9p 13 in a region that exhibits loss of heterozygosity or homozygous deletion in several different tumor types. Together, these results indicate that loss of topors SUMO ligase activity for Top1, p53, or other substrates can predispose a subject to malignancy. Given the substrates involved, protein sumoylation is important in the course of tumorigenesis and, accordingly, altered in human cancer.

Furthermore, overexpression of topors in cervical cancer cell lines leads to cell death. Thus, a lack of topors in cancer cells contributes to the selection and persistence of mutant phenotype and progression to tumorigenesis. Thus, topors can be added directly to tumor cells to induce cell death. Topors can also be added to tumors to make the tumor cells more sensitive to anti-cancer therapies, such as radiation and chemotherapy.

Additionally, it was shown that topors functions as an E3-type ubiquitin ligase an E3-type SUMO ligase for topoisomerase and p53. Thus, topors is a dual function ubiquitin and SUMO ligase. Recombinant topors enhances formation of polyubiquitin conjugates by specific E2 ubiquitin enzymes in vitro, with the RING domain necessary and sufficient for this activity. While topors-induced ubiquitination of bacterially expressed top1 was unable to be detected in vitro, similar assays using Ubc9, SAE1/SAE2, and SUMO-1 indicate that topors stimulates formation of top1-SUMO-1 conjugates by Ubc9. Additional in vitro studies indicate that topors enhances Ubc9-mediated sumoylation of p53 but not IkBα, indicating that topors does not non-specifically increase Ubc9 activity. Stimulation of top1 sumoylation by topors does not require the topors RING domain. Instead, this activity maps to the 536-704 region, which contains a nuclear localization sequence and is within the top1-binding region. Ectopic expression of topors in HeLa cells increases formation of SUMO-2 conjugates.

Accordingly, one aspect of the present invention relates to an anti-topors antibody and use thereof in the detection and modulation of topors activity. For the purposes of the present invention, the term "antibody" includes polyclonal and monoclonal antibodies, chimeric, single chain, and humanized antibodies, as well as Fab fragments, including the products of a Fab or other immunoglobulin expression library. As is conventional in the art, "monoclonal antibodies" means a substantially homogenous population of antibodies to a particular antigen. Such antibodies be obtained by any technique that provides for the production of antibody molecules by continuous cell lines in culture. Monoclonal antibodies can be obtained by methods well-known in the art.

In contrast to monoclonal antibodies, "polyclonal antibodies" are a group of heterogeneous antibodies produced by different B lymphocytes in response to the same antigen, wherein different antibodies in the group recognize different parts of the antigen.

Of particular use in accordance with the present invention are antibodies that bind to topors and completely inhibit topors activity with respect to topors binding to Top1, p53, or any other protein with which topors interacts. In particular embodiments, the topors antibodies exhibit a specific binding affinity for the topors protein alone. The term "specific binding affinity" means that the antibody or antibody fragment binds to target compounds (i.e., topors) with greater affinity than it binds to other compounds under specified conditions. Antibodies or antibody fragments having specific binding affinity to a compound can be used to inhibit the function of that compound by contacting it with the antibody or antibody fragment under conditions such that an immunocomplex forms, inhibiting the function of the compound conjugated to the antibody or antibody fragment. Alternatively, the antibody can be used to bind the topors protein and identify the presence of topors in a given sample. Moreover, topors antibodies of the present invention find application in research involving the further investigation of cellular role of topors and related nuclear proteins.

Monoclonal antibodies can be prepared according to the general hybridoma methods of Kohler and Milstein ((1975) *Nature* 256:495-497), the trioma technique, the human B-cell hybridoma technique (Kozbor, et al. (1983) *Immunology Today* 4:72) or the EBV-hybridoma technique (Cole, et al. (1985) *Monoclonal Antibodies and Cancer Therapy*, Alan R. Liss, Inc. pp. 77-96). Antibodies utilized in the present invention can also be polyclonal antibodies, although monoclonal antibodies are generally desirable because they can be reproduced by cell culture or recombinantly, and can be modified to reduce their antigenicity. Polyclonal antibodies can be raised by any standard protocol by injecting a production animal with an antigenic composition containing topors. See, e.g., Harlow and Lane (1933) *Antibodies: A Laboratory Manual*, Cold Spring Harbor Laboratory).

In accordance with one embodiment of the present invention, a topors antibody is used to detect the presence or absence of topors in various screening assays, which may lead to improved diagnosis and treatment of cancer and other topors-related diseases. In general, an assay of the invention involves detecting the presence or absence of topors in a sample such as a biopsy sample, tissue, or cell from a subject having or suspected of having a cancer (e.g., a cancer disclosed herein), wherein the absence of topors is indicative of cancer. When employing an antibody to detect topors, particular embodiments embrace an antibody that is detectably labeled. Most desirably, the antibody is detectably labeled and easily assayed, such as with fluorescence. If the topors antibody binds to topors, then topors is present in the sample, indicating that cancer is not present. Conversely, absence or decreased levels of topors is indicative of a cancer. Antibody-based assays of the present invention can be carried out using any suitable well-known method including, but not limited to, ELISA, western blot analysis, dot blots and the like. Similarly, the presence or absence of topors can be detected based upon the presence or absence of nucleic acid molecules (e.g., RNA transcript) encoding topors, wherein the absence of such nucleic acid molecules is indicative of a cancer. As exemplified herein, primers that hybridize to a nucleic acid molecule encoding topors can be used in such methods as RT-PCR to detect topors nucleic acid molecules. Alternatively, conventional methods such as northern blot analysis can be employed.

In certain embodiments, the amount of topors present in a sample is determined. Detection of the relative and/or absolute amount of topors allows diagnosticians to determine if the levels of topors are normal or depressed. Depressed levels of topors is indicative of cancer or could indicate that uncontrolled cellular proliferation does not currently exist, but has a higher chance of occurring in that subject in the future. This use of the topors antibody leads to another embodiment of the invention, which is using the antibody screen to predict a subject's chances of contracting an uncontrolled proliferating cellular disease, such as cancer. A topors antibody screen allows the testing of various tissues to determine whether the presence of topors is diminished. If diminished levels of topors protein are found, a treating physician could take proactive steps to prevent the cancer, such as administering topors to the subjects via the embodiments described herein.

In a related embodiment, a genetic screen is employed to identify subjects with higher susceptibility to tumorigenesis based on loss of normal levels of topors DNA or RNA before cancer or any other disease related to the loss of topors manifests in a subject. Subjects with mutated DNA or RNA encoding topors would have a greater chance of those cells not producing topors or producing a nonfunctional form of topors. As used herein, "mutated" refers to an alteration of the primary sequence of a nucleic acid molecule or protein such that it differs from the wild-type or naturally occurring sequence. The genetic screen can be carried out by methods well-known in the art, such as isolating a gene using restriction enzymes and then sequencing the gene or examining the gene for polymorphisms. Examples of such polymorphisms can include, e.g., SNPs identified under GENBANK Accession Nos. rs28372759, rs17857515, rs17855104, rs17855103, rs17218354, rs13297394, rs13289143, rs12553445, rs12376833, rs12348918, rs12236253, rs10971022, rs10971021, rs10971020, rs10971019, rs10695262, rs9919071, rs7851560, rs5897511, rs3814518, rs1804959, rs1197247, rs1197246, rs682071, rs628425, rs588127, rs560232, and rs15014.

Other aspects of the invention also emply the topors antibody as a screen in a similar manner, wherein samples are examined for higher than normal (rather than lower) physiological levels of topors. The screen would be used to detect a disease in which topors is overexpressed in tissues, such as diseases wherein cells are subject to high levels of cellular stress. Data have revealed the relevance of post-translational modification of proteins via covalent attachment of SUMO in cell cycle progression, stress response and signal transduction. p53 functions in response to a variety of cellular stresses. While the beneficial anticancer effects of p53 are well-established, p53 has also been implicated in human aging. (Sharpless, et al. (2002) *Cell* 110(1):9-12).

If the screen determined that the cellular level of topors were elevated, another aspect of the invention would instruct the administration of topors antibody in vivo to the location of the elevated topors levels, wherein the topors antibody would bind topors. In this regard, by controlling the level of topors, which binds to p53, cellular aging could be manipulated, particularly if it were previously exposed to a stress that raised the level of p53. An important aspect of this embodiment is to maintain monitoring of and control over the level of topors in the cells because depressed levels of topors lead to uncontrolled cellular proliferation.

A kit for prediction and diagnosis of diseases related to uncontrolled cellular proliferation, such as cancer, by using the topors antibody for all of the methods described above is also contemplated. A kit for this purpose would contain the topors antibody and instructions for use. Since the antibody can be used in multiple ways to carry out the multiple methods described, the directions could indicate each of the ways in which the screening method can be used. The kit could also contain reagents, a detectable label for the antibody, tubes, trays, and other items associated with the carrying out of the screen.

Yet another embodiment of the present invention embraces a method of using topors as a tumor suppressor protein. In accordance with this embodiment, both topors and the topors antibody can be used to modulate the DNA repair process. In general, a therapeutically effective amount of topors or topors antibody is administered in a pharmaceutically acceptable carrier. A "pharmaceutically acceptable carrier" is one that is non-toxic to recipients at the dosages and concentrations employed and is compatible with other ingredients of the formulation. For example, the formulation would not contain any substances that are known to be deleterious to topors. The carrier can contain additives such as substances that enhance isotonicity and chemical stability. The additive materials can include buffers such as phosphate, citrate, succinate, acetic acid, and other organic acids or their salts; antioxidants such as ascorbic acid; low molecular weight (less than about fifteen residues) polypeptides, proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, trehalose, glucose, mannose, or dextrins; chelating agents such as EDTA; sugar alcohols such as mannitol or sorbitol; counter-ions such as sodium; and/or nonionid surfactants such as polysorbates, poloxamers, or PEG. The final topors or topors antibody preparation can be a liquid or lyophilized solid.

In accordance with the therapeutic method of the invention, topors protein is used to stop the continued production of DNA in a cell with mutated DNA. In contrast, if a normal and/or advantageous cell has lost the ability to replicate due to an over-abundance of topors, topors antibody is added to bind up some of the excess topors to allow the cell to continue replicating. The topors or topors antibody can be administered generally through a variety of routes of administration, or locally to the site of uncontrolled cellular proliferation.

"Therapeutically effective amount" refers to that amount of the compound that results in amelioration of symptoms or a prolongation of survival of a subject. A therapeutically effective amount of topors in the present invention will generally be in the range of about 0.01 µg/kg to about 100 mg/kg per day. Desirably, from 0.1 to 1 µg/kg. A clinician will administer topors formulations of the invention until a dosage is reached that improves uncontrolled proliferating cells condition, taking into account the usual factors the specific disorder being treated and the severity of the disorder, the specific composition administered, the age, weight, general health, and gender of the subject, and other factors individual to the subject. The progress of this therapy can be monitored by usual assays for detecting the disorder. For example, if the disorder is cancer, the progress of cancer treatment can be monitored through blood test, CAT scans, PET scans, urinalysis, and other known methods.

"Administration" means administration of the therapeutic compound. Administration can be carried out orally, parenterally, osmotically, or topically in unit dosage formulations containing carriers, adjuvants, diluents, vehicles, or combinations thereof. "Parenteral" includes infusion as well as subcutaneous, intravenous, intramuscular, and intrasternal injection. Parenterally administered aqueous compounds can be formulated with dispersing, wetting, or suspending agents. Use of diluents or solvents are also acceptable if they do not significantly alter the pharmaceutical effectiveness of the topors being administered. Among the acceptable diluents or solvents employed are water, saline, Ringer's solution, buffers, monoglycerides, diglycerides, fatty acids such as oleic acid, and fixed oils such as monoglycerides or diglycerides. Materials can be used to slow the absorption of parenterally administered compounds, such as suspensions of crystalline, amorphous, or otherwise water-insoluble forms of the compound.

Oral administration of solid dosages include capsules, tablets, pills, powders, and granules. Here again, diluents and buffering agents such as sucrose, lactose, starch, talc, aluminum hydroxide, calcium silicates, polyamide powder, tableting lubricants, and tableting aids are acceptable. Excipients like talc, aluminum hydroxide, calcium silicate, polyamide powder, can be added to powders and sprays. Potential forms of liquid dosage include emulsions, microemulsions, solutions, suspensions, syrups, and elixirs. Topical administration can occur through the use of ointments, pastes, creams, lotions, gels, powders, solutions, sprays, inhalants, and/or transdermal patches, all of which can also include excipients. For administration by inhalation, the compounds for use according to the present invention can be delivered in the form of an aerosol spray presentation from pressurized packs or a nebuliser, with the use of a suitable propellant, like dichlorodifluoromethane, trichlorofluoromethane, dichlorotetrafluoroethane, carbon dioxide or other suitable gas.

Furthermore, administration can be local or systemic, depending on the location of the cells or tissues to be treated. For example, the drug can be administered in a targeted drug delivery system, such as in a liposome coated with a specific antibody, targeting the affected tissue. The liposomes will be targeted to and taken up selectively by the afflicted tissue. It is also contemplated to administer the pharmaceutical composition locally with an implant or device.

An additional aspect of the present invention contemplates the addition of topors to uncontrolled proliferating cells, not just for the correction of the nucleic acid or apoptosis by allowing the camptothecins to work effectively, but also to sensitize the cancerous cells to traditional cancer therapy treatments. The topors makes the cells ready to either repair DNA damage or die. The addition of chemotherapy or radiation further weakens the cells and likely causes those cells to self-destruct.

Yet another embodiment of the present invention involves the use of the topors nucleic acid molecule and protein to develop small molecule inhibitors for topors ubiquitin and SUMO ligase activities. Both the ubiquitination and sumoylation activities assist in controlling the replication of the cells and the small molecule inhibitors allow for further manipulation of these processes. The small molecule inhibitors can be developed through methods known in the art given the knowledge of the sequence and function of topors as a tumor inhibitor.

Moreover, the nucleic acid molecule encoding topors can be used in a gene therapy approach to replace or re-introduce topors DNA as the therapeutic gene into the desired location in a subject or in vitro. Desirably, the area of delivery would be a tumor cell and a topors nucleic acid molecule would be enclosed in a construct, such as a vector. The vector could be a viral vector, or a nonviral vector, such as a liposome. Post-translational processing of the DNA can occur after the DNA has been translated by the affected cell.

By "nucleic acid molecule" is meant both RNA and DNA including cDNA, genomic DNA, plasmid, DNA, condensed nucleic acid, or nucleic acid formulated with compounds able to prolong the localized bioavailability of a nucleic acid. In one embodiment, the nucleic acid molecule administered is plasmid DNA that is a "vector".

The term "vector" refers to a construct composed of genetic material designed to direct transformation of a targeted cell, as well as, various regulatory elements for transcription, translation, transcript stability, replication, and other functions as are known in the art. "Post-translational processing" means alterations made to the expressed gene product, including addition of side chains such as carbohydrates, lipids, inorganic or organic compounds, and cleavage of targeting signals or propeptide elements. The vector can include one or more genes in a linear or circularized configuration, or a plasmid backbone.

An "expression vector" is a vector that allows for production of a product encoded for by a nucleic acid sequence contained in the vector. For example, expression of a particular growth factor protein encoded by a particular gene. A "viral vector" is a vector whose original form is as the genomic material of a viral particle. Viral vectors include retrovirus, adenovirus, adeno-associated virus, and lentivirus.

The term "promoter" refers generally to transcriptional regulatory regions of a gene, which may be found at the 5' or 3' side of the coding region, or within the coding region, or within introns. A promoter is usually DNA regulatory region capable of binding RNA polymerase in a cell and initiating transcription of a downstream coding sequence. The typical 5' promoter sequence is bounded at its 3' terminus by the transcription initiation site and extends upstream to include the minimum number of bases or elements necessary to initiate transcription at levels detectable above background. Within the promoter sequence is a transcription initiation site is found within the promoter sequence.

The term "therapeutically effective amount" with respect to a vector refers to a dose of vector and level of gene expression resulting from the action of the promoter on the nucleic acid cassette when introduced into the appropriate cell type that will produce sufficient protein, polypeptide, or antisense RNA to either increase the level of protein production, decrease or stop the production of a protein, inhibit the action of a protein, inhibit proliferation or accumulation of specific cell types, or induce proliferation or accumulation of specific cell types. The dose will depend on the protein being expressed, the promoter, uptake and action of the protein or RNA.

In a further embodiment, topors antibody could be used in a vaccine to treat diseases associated unchecked cell proliferation. The gene therapy system can be inducible, meaning that the genes are only transcribed when an outside stimulus is applied. Promoters can also be used in the vector.

The invention is described in greater detail by the following non-limiting examples.

EXAMPLE 1

Generation of Anti-Topors Polyclonal Antibodies

Figure 2:
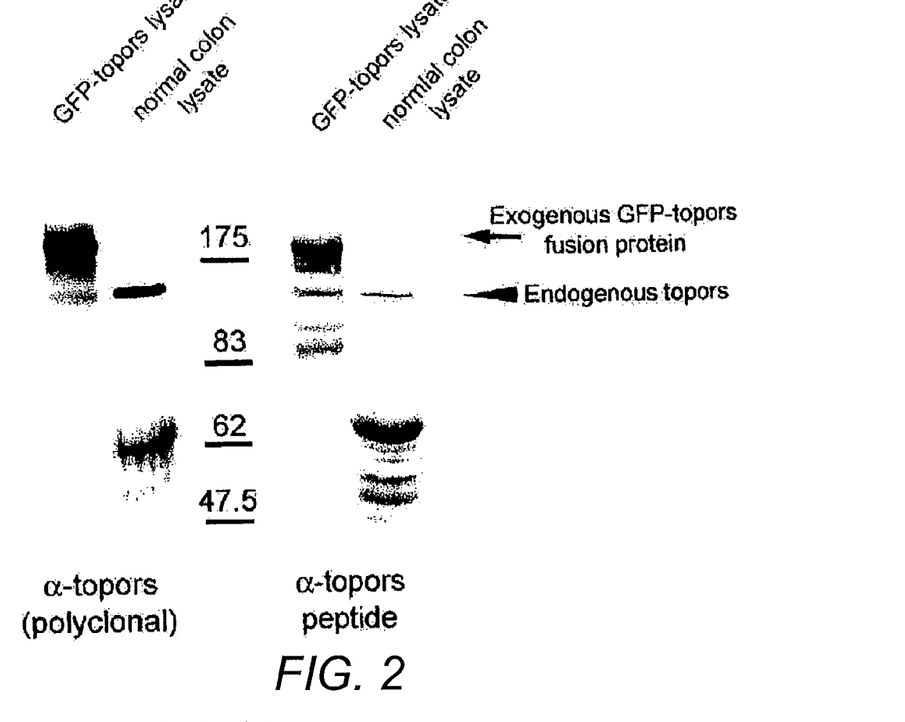
FIG. 2 demonstrates that a polyclonal topors antibody recognizes both recombinant and endogenous topors. 50 µg of HeLa cell lysates obtained from cells transiently transfected with a GFP-topors plasmid and 100 µg of colon tissue lysate were loaded in lanes 1 and 2 in each panel, respectively. Immunoblot analyses were performed with a topors polyclonal antibody. Migration of GFP-topors and endogenous topors are indicated.

Topors cDNA was cloned into pKG, an inducible yeast expression vector, to obtain purified GST-topors from a eukaryotic source. The purified recombinant GST-topors protein was used to immunize rabbits. Similarly, a peptide representing residues 870-889 (VYEGKATDTTKHH-KKKKKKH; SEQ ID NO:1) of topors was used to generate antibodies directed towards this region of the protein. Immunoblot analyses indicated that both antibodies recognized a recombinant GFP-topors protein in HeLa cell lysates (FIG. 2). Furthermore, both antibodies recognized a predominant band migrating at ~135 $M_r$ in normal bladder, colon, prostate, endometrium, kidney, lung, stomach and testicles tissue lysates (FIG. 2). This band was also recognized, albeit with lower affinity, by an antibody recognizing a C-terminal peptide of topors. Neither the GFP-topors nor endogenous topors bands were visualized in control experiments using pre-immune rabbit serum or secondary antibody alone.

The serum from rabbits injected with the full-length GST-topors protein yielded a better signal in immunoblot assays (FIG. 2), and this serum was used in all subsequent topors immunoblot experiments. In eukaryotic cells, topors migrated slower than predicted based upon calculated molecular weight (predicted molecular weights of GFP-topors and endogenous topors were 146 and 119 kDa, respectively, with these proteins migrating at 170 and 135 $M_r$, respectively). This aberrant migration may have been due to conjugation with SUMO proteins.

EXAMPLE 2

Differential Expression of Topors Protein

Figure 3:
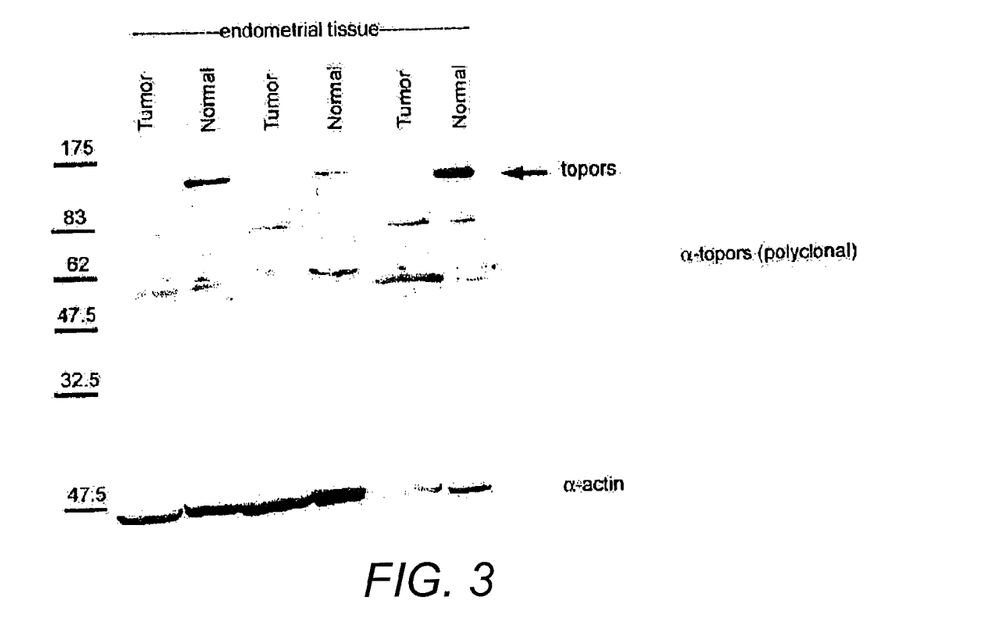
FIG. 3 shows topors protein levels in normal and tumor endometrial tissues. Each lane contains 10 µg of protein. Immunoblot analyses were performed using a topors polyclonal antibody. The blots were stripped and reprobed with actin monoclonal antibody.
Figure 4:
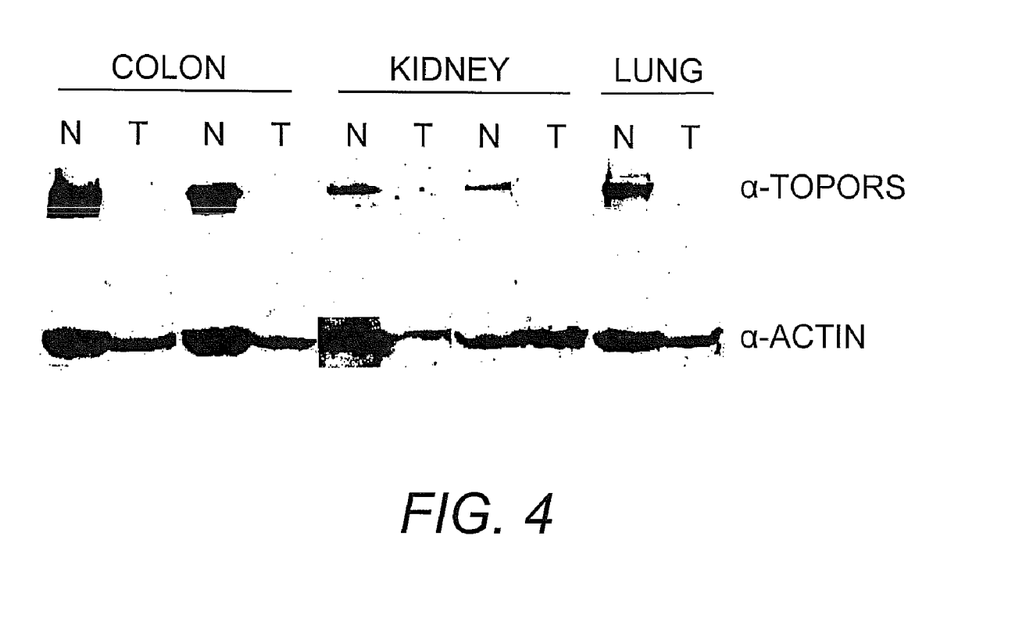
FIG. 4 shows topors protein levels in normal and tumor tissues from colon, kidney and lung. Ten µg of protein was loaded in each lane and immunoblot analyses was carried out using a topors polyclonal antibody. The blots were then analyzed with actin monoclonal antibody.

The topors protein was not detected in lysates from several different tumor cell lines. In this regard, in matched normal and tumor human tissue specimens, the topors protein was detectable only in normal tissues (FIGS. 3 and 4). As a control, the same blots were reprobed with an actin monoclonal antibody, with results indicating that actin levels were similar, excluding unequal loading as a reason for the difference in topors levels between normal and tumor tissues. In addition, overexpression of topors in a cervical cancer cell line was found to result in cell death. Based on these results, it is contemplated that expression of topors in cancer cells leads to alterations in the sumoylation of top1 and other proteins that are required for uncontrolled proliferation, resulting in tumor cell death.

EXAMPLE 3

Differential Expression of Topors mRNA

Figure 5:
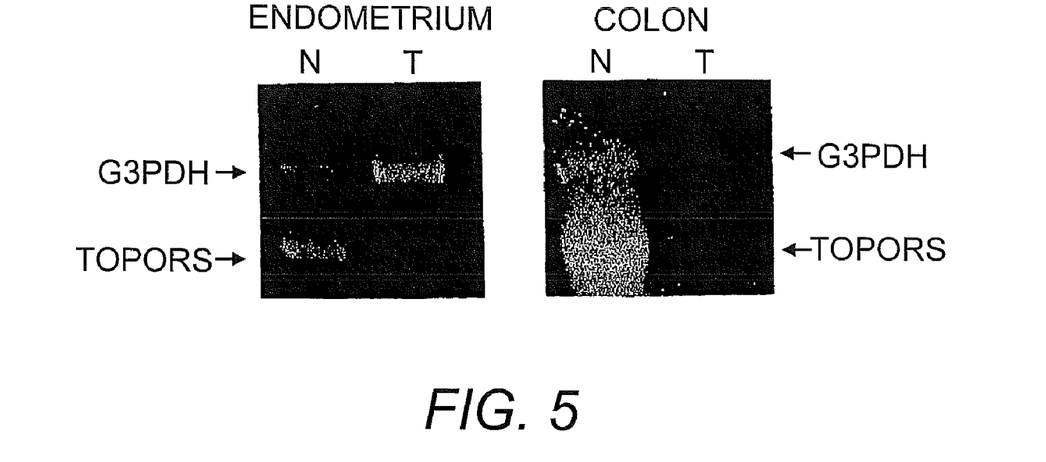
FIG. 5 shows topors mRNA levels in normal and tumor tissues. Total RNA was isolated from tissue samples and analyzed simultaneously for topors and G3PDH mRNA expression using specific primers for each gene and RT-PCR.

In two specimens where topors protein levels were undetectable in the tumor, little, if any, topors mRNA was detected by RT-PCR, whereas G3PDH (glyceraldehyde-3-phosphate dehydrogenase) mRNA bands were similar in tumor and normal tissues (FIG. 5). The significance of this finding is that not all mRNA was lacking in tumor cells, because non-topors mRNA remained at normal physiological levels.

EXAMPLE 4

Topors Functions as an E3-Type SUMO Ligase

Topors is homologous in the RING domain to proteins implicated in conjugation of ubiquitin and SUMO, such as MDM2 and BRCA1. Previously, it has been shown that topors binds to the N-terminus of top1. Furthermore, top1 has been shown to be a substrate for ubiquitin- and SUMO-conjugation following cellular treatment with CPT. Topors also redistributes from PML (promyelocytic leukemia) nuclear bodies to a diffuse nuclear localization when exposed to CPT. When incubated with a HeLa cell fraction containing SAE1/SAE2, purified SUMO-1, and purified Ubc9, minimal top1-SUMO conjugates could be detected using Top1 and SUMO antibodies.

The present experiments show that GST (Glutathione S-Transferase)-topors binds to the SUMO-conjugating enzyme (Ubc9), whereas GST does not bind. Furthermore, they also show that topors enhances top1 sumoylation in vitro. Using purified components of the sumo conjugation system as well as purified top1 and topors, top1-SUMO conjugates were detected. Removing any of the sumoylation components or topors abrogated top1 sumoylation. Taken together, these data show that topors functions as an E3-type SUMO ligase, catalyzing top1 sumoylation.

EXAMPLE 5

Topors Functionality and Cellular Behavior

Topors functions as an E3 ubiquitin ligase and as an E3-type SUMO ligase for Top1, both of which act to regulate the replication of DNA in a given cell. This analysis was carried out using reactions containing 400 ng E1, 200 ng of various E2 proteins, 3 µg of ubiquitin, and either ~100 ng GST-topors or GST. Reaction products were resolved by SDS-PAGE under reducing conditions. Migration of probable poly-ubiquitin chains was determined. All E2s were active as assessed by thiolester formation.

Topors also activates sumoylation of p53, but not IkBα. This finding is significant because it is known to be sumoylated and IkBα is a check to ensure that topors does not activate p53 and Ubc9 nonspecifically. Reaction products were analyzed using monoclonal anti-p53 and polyclonal anti-IkBα antibodies. Reactions contained increasing amounts of E1 and Ubc9 in order to demonstrate sumoylation of IkBα by Ubc9 in the absence of topors. In addition, it was shown that topors increases SUMO-2 conjugates in mammalian cells Acute promyelocytic leukemia, a type of cancer affecting the blood, is characterized by an abnormal block in the development of stem cells. It has now been discovered that topors localizes in nuclear bodies associated with promyelocytic leukemia (PML) oncogenic domains. In these experiments HeLa cells were immunostained with antibodies recognizing both topors and PML. Separate and merged fluorescent images from a representative cell were analyzed. PML nuclear bodies are nuclear depot sites, which are disrupted in cells from patients with promyelocytic leukemia with t (15; 17). Topors relocalized to the nucleoplasm after DNA damage. Moreover, DRB and CPT induce rapid dispersion of topors but not PML from nuclear bodies. In these experiments, HeLa cells expressing GFP-topors or GFP-PML were imaged before and after treatment with 0.1% DMSO, 10 μM DRB, 10 μM CPT, or 30 μM cycloheximide for thirty minutes.

EXAMPLE 6

Loss of Topors Protein and mRNA Expression in Human Colon Cancers

It was difficult to detect topors expression in several cancer cell lines (U-937, HeLa, Hct116, DU145, MCF7), but not in normal tissues, including bladder, colon, endometrium, kidney, lung, and prostate. To further investigate this phenomenon, a series of matched and unmatched specimens of normal colon tissue and colon tumors (8 adenocarcinoma, 1 adenoma) was analyzed for expression of the topors protein.

Using the topors antibody raised against the full-length protein, topors protein expression was surveyed in cancer cell lines and in human normal and cancer tissues (obtained from the CINJ Tissue Retrieval Core and the Cooperative Human Tissue Network). Gross diagnosis of the tissues was reconfirmed by H&E staining. After thawing, frozen tissue specimens were weighed and cut into approximately 0.1 gram aliquots. For protein analysis, an aliquot was homogenized in 1 ml of buffer containing 50 mM Tris pH 7.2, 150 mM NaCl, 1 mM PMSF, 0.5 μg/ml leupeptin, and 1 μg/ml pepstatin. SDS was then added to 1%, the lysates incubated at 95° C. for 10 minutes, then centrifuged at 13,000× g for 10 minutes. SDS-PAGE sample buffer was added to the supernatant, which was heated at 95° C. for 5 minutes, then loaded onto a polyacrylamide gel. The samples were first analyzed for α-actin expression, then diluted in lysis buffer as needed to obtain relatively equal concentrations of this protein. Alpha-actin-normalized samples were then subjected to SDS-PAGE and immunoblot analyses using the topors antibody.

Figure 6A:
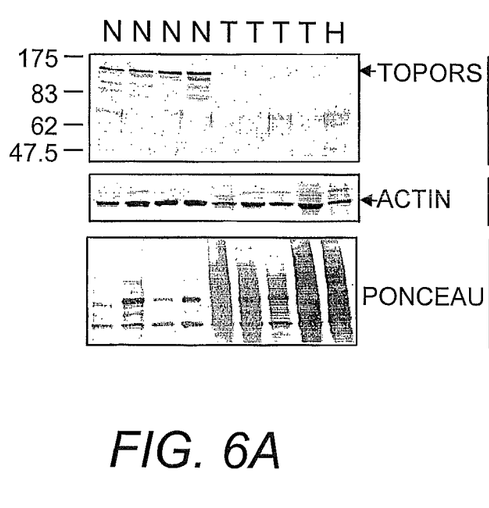
FIG. 6 is an image of normal and tumor samples subjected to SDS-PAGE and immunoblot analysis demonstrating a loss of topors protein expression in colon cancers.
Figure 6B:
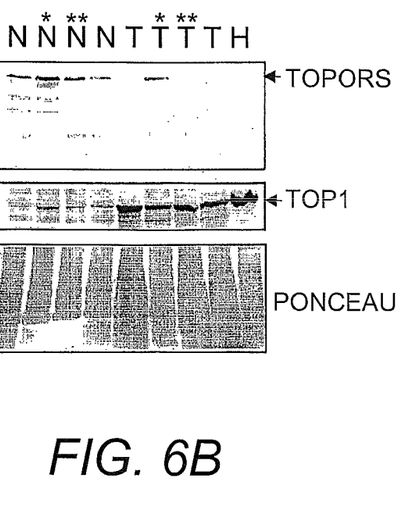

FIGS. 6A and 6B shows the results obtained with 2 sets of normal (N) and colon cancer (T) tissues. In FIG. 6B, "H" represents ~20 °g of lysate obtained from Hct116 colon cancer cells, and lanes with asterisks represent matched normal and cancer tissues obtained from the same patient. Note that in the single asterisk case, the tumor tissue was adenoma, whereas the tumor tissue was adenocarcinoma in all other cases. Ponceau staining of each blot is shown, as well as results obtained by immunoblot analysis with α-actin (FIG. 6A) or top1 (FIG. 6B) antibodies.

When the samples were normalized for α-actin expression, topors protein expression was detectable in all the normal colon specimens, with expression levels greater in some specimens than in others (FIG. 6). Topors protein expression was also detectable in the benign adenoma specimen (FIG. 6B, T*). By contrast, topors protein expression was either low or undetectable in several colon cancer specimens. Fourteen colon cancer specimens were analyzed and topors protein expression was detected in only two of those specimens. Furthermore, the relative decrease in topors expression in cancer versus normal tissues is likely underestimated using the α-actin normalization approach, since Ponceau staining indicates that this approach typically results in significantly more protein being loaded in cancer tissue lanes (FIG. 6). In addition, these results cannot be explained by decreased extraction of nuclear proteins from cancer versus normal tissues, since top1 levels were typically higher in colon cancer versus normal colon tissues (FIG. 6B).

EXAMPLE 7

Differences in Topors mRNA Expression in Matched Normal and Cancer Colon Tissue

Topors mRNA expression was also analyzed in a series of 10 matched colon tumor/normal specimens (9 adenocarcinoma, 1 adenoma), using a semi-quantitative multiplex RT-PCR assay. RNA extraction from matched normal colon (N) and colon cancer (T) tissues was performed using the PURE-SCRIPT RNA Isolation Kit (Gentra Systems, Inc.). Topors primers included forward primer 5'-CGA GCA CCA GCA CGA TAA AGA GTT CGT C-3' (SEQ ID NO:2) and a reverse primer 5'-TCC TGC CGA CAC CGA CCT AGC TTT C-3' (SEQ ID NO:3). The PCR was performed using following cycles, 50° C. for 1 hour; 94° C. for 5 minutes; followed by 30 cycles of 94° C. for 30 seconds, 65° C. for 30 seconds, 68° C. for 1 minute; followed by 68° C. for 2 minutes. As a control for mRNA quantities, G3PDH primers were included in the reaction using forward primer 5'-TGA AGG TCG GAG TCA ACG GAT TTG GT-3' (SEQ ID N0:4) and reverse primer 5'-CAT GTG GGC CAT GAG GTC CAC CAC-3' (SEQ ID NO:5). PCR products were visualized by agarose gel electrophoresis, followed by ethidium bromide staining. Note that in specimen 1545 the tumor is a benign adenoma rather than adenocarcinoma, which is the case for all other specimens.

Figure 7:
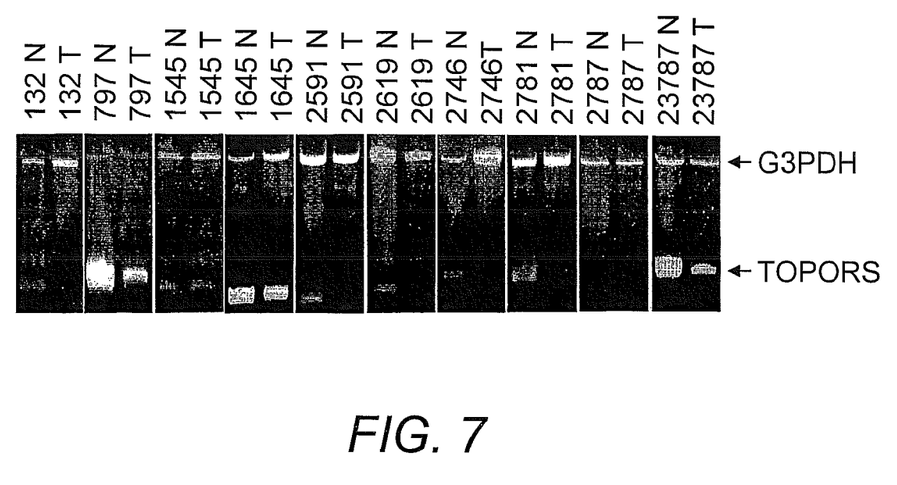
FIG. 7 is an agarose gel showing differential expression of topors mRNA in matched normal and colon cancer. The numbers at the top of each panel refer to a matched number specimen.
Figure 8:
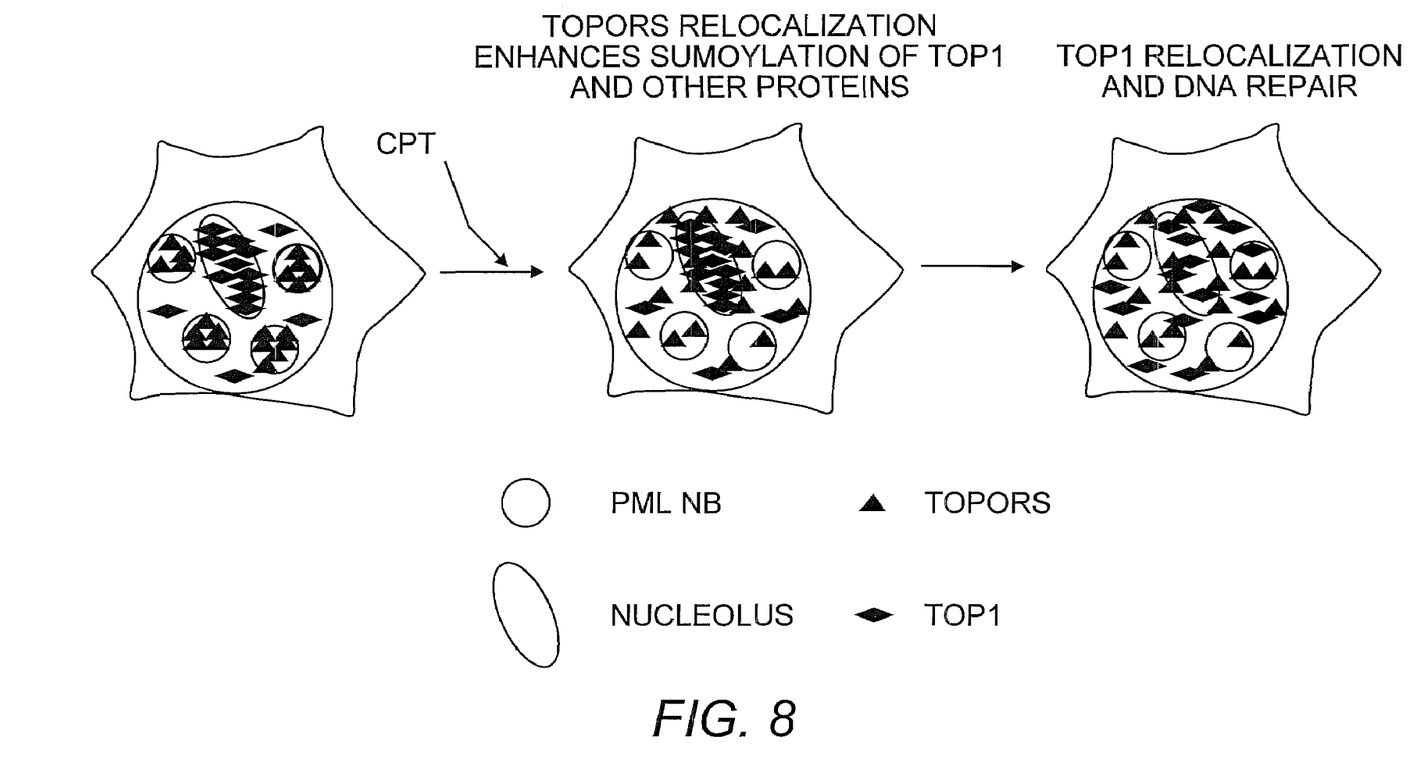
FIG. 8 is a cartoon depiction of a model for the cellular function of topors. PML NB stands for promyelocytic leukemia nuclear bodies. CPT stands for camptothecin.

Similar to results obtained with the topors antibody, topors mRNA expression was also reduced in 7 of 10 colon cancer tissues relative to matched normal tissues (FIG. 7). Furthermore, topors mRNA expression was compared to topors protein expression for two matched specimens. Both topors protein and mRNA expression were similar in the normal and tumor (adenoma) tissue in one case (denoted as a single asterisk in FIG. 6B, and as 1545N and T in FIG. 7), whereas in the other case, both topors protein and mRNA expression were reduced in the cancer relative to normal tissue (double asterisk in FIG. 6B, 132N and T in FIG. 7). Thus, for these two cases, there was a correlation between topors protein and mRNA expression. Topors relocalization enhances sumoylation of Top1 and other proteins based on the model of the present invention (See FIG. 8), which leads to Top1 relocalization and ultimately, DNA repair.

EXAMPLE 8

Topors mRNA is Widely Expressed in Human Tissue

Figure 9:
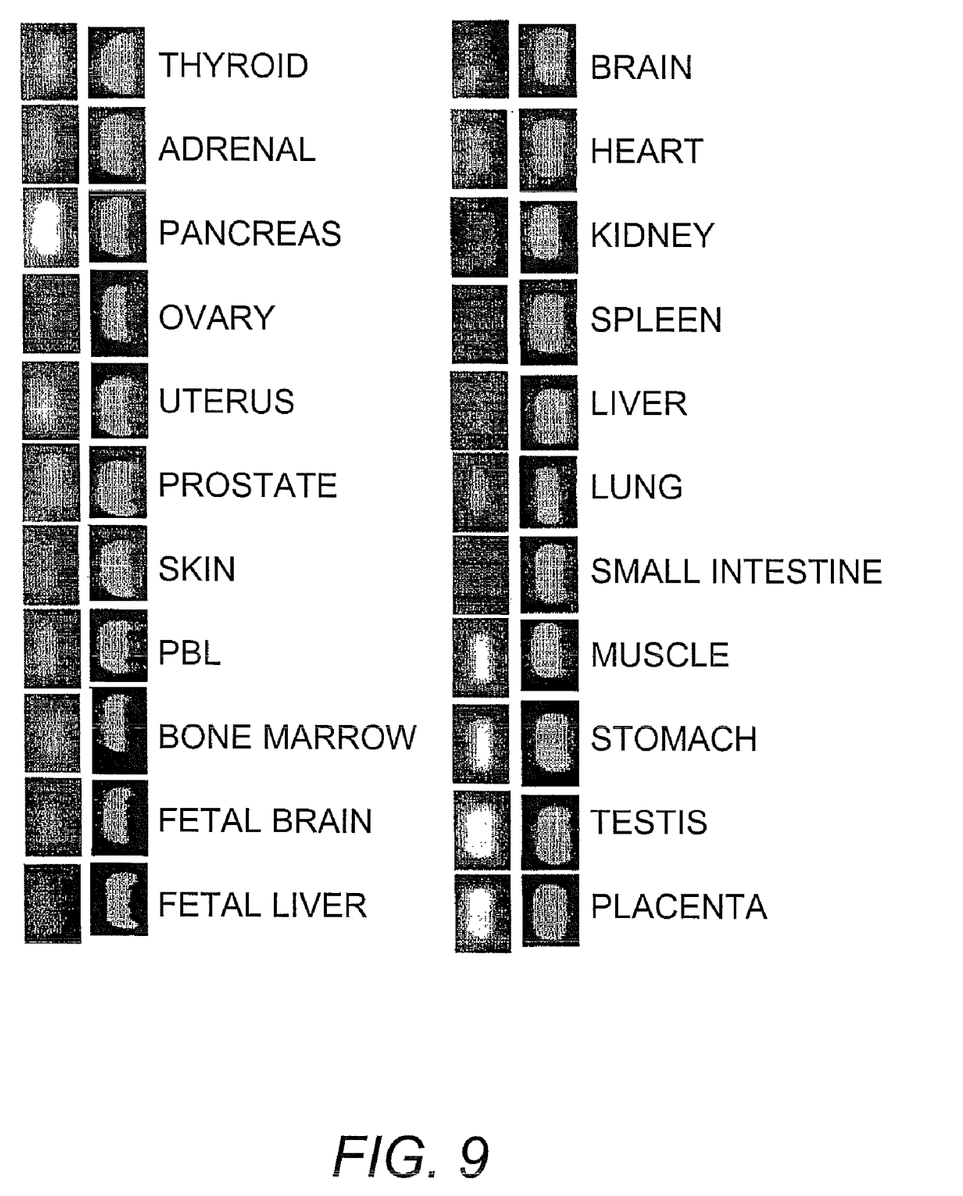
FIG. 9 is an agarose gel showing topors (lower panel) mRNA and β-actin (upper panel). Topors mRNA is expressed in most normal tissues.

It has been suggested that topors mRNA is expressed at relatively low levels in human U-937 leukemia cells. To gain insight into topors biology, topors mRNA expression in human tissues was analyzed using an alpha-actin-normalized cDNA panel. The results indicated that topors mRNA expression was detectable in most human tissues, with relatively high expression observed in the testis, placenta, and pancreas (FIG. 9). In FIG. 9, human tissue cDNAs normalized for beta-actin mRNA expression were obtained from Origene Technologies and analyzed by PCR using topors (lower panel) and alpha-actin (upper panel) primers. PCR products were visualized by ethidium bromide staining of agarose gels. Serial dilutions over a 4-log range were used to establish that the resulting band intensities were linear with respect to input cDNA. Results obtained with undiluted cDNA are shown for the topors primers and for a 1:10 dilution for the actin primers.

EXAMPLE 9

Forced Expression of Topors Inhibits Thymidine Incorporation in Cancer Cells

To further investigate the relative lack of topors expression in cancer tissues and cell lines, the effects of overexpression of topors on the proliferation of HeLa cells was analyzed using transient transfections and a thymidine incorporation assay. Exponentially growing HeLa cells were transfected with 5 µg of either the pEGFP (GFP) or pEGFP-topors (GFP-topors) plasmid using a LIPOFECTAMINE-based method. Twelve hours after transfection, 1 U-937 µCi/ml $^3$H-thymidine and 150 nM cold thymidine were added to the media. After an additional 24 hours the cells were washed 4 times with ice cold PBS and fixed in methanol for 30 minutes at 4° C. After removal of methanol and drying, the cells were solubilized in a solution of 0.25% NaOH and 0.25% SDS. After neutralization with 1 N HCl, radioactivity was quantitated by scintillation counting. Results were presented as mean and standard deviations of triplicate samples and were expressed relative to mean disintegrations per minute obtained with non-transfected HeLa cells analyzed concurrently (Control). The difference between the mean GFP value (72%) and the mean GFP-topors value (36%) was statistically significant ($p<0.05$, unpaired two-way t-test).

The results indicate that transfection with pEGFP-topors significantly decreases thymidine incorporation compared to transfection with pEGFP. It is possible that the results of this experiment underestimate the anti-proliferative effects of topors overexpression, since about 50% of HeLa cells are routinely observed expressing GFP-topors after transfection with the pEGFP-topors plasmid.

What is claimed is:

1. A method for diagnosing cancer in a subject comprising assaying a colon, kidney, or endometrial tissue sample from a subject for the presence or absence of topors, wherein the absence of topors in the sample indicates that the subject has cancer, and wherein said cancer is selected from the group consisting of colon cancer, endometrial cancer, and kidney cancer.

2. The method of claim 1, wherein topors is detected using an antibody that binds topors.

* * * * *

UNITED STATES PATENT AND TRADEMARK OFFICE
CERTIFICATE OF CORRECTION

| | | |
|---|---|---|
| PATENT NO. | : 7,632,650 B2 | Page 1 of 1 |
| APPLICATION NO. | : 11/671041 | |
| DATED | : December 15, 2009 | |
| INVENTOR(S) | : Eric H. Rubin | |

It is certified that error appears in the above-identified patent and that said Letters Patent is hereby corrected as shown below:

At column 1, lines 11 and 12, please delete "in the course of research sponsored" and insert --with government support under 5R01CA99951-8 awarded--

At column 1, lines 12 and 13, please delete "(NIH Grant No. GM59170)"

At column 1, line 13, please delete "may have" and insert --has--

Signed and Sealed this
Sixth Day of November, 2012

David J. Kappos
*Director of the United States Patent and Trademark Office*